United States Patent
Baker et al.

(10) Patent No.: US 6,742,522 B1
(45) Date of Patent: Jun. 1, 2004

(54) SURGICAL INCISE DRAPE

(75) Inventors: Dennis L. Baker, Houlton, WI (US); John E. Bruno, Lindstrom, MN (US); Patricia A. Eull, Mahtomedi, MN (US); Dietmar Schlei, Hudson, WI (US); Matthew T. Scholz, Woodbury, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 09/400,612

(22) Filed: Sep. 20, 1999

Related U.S. Application Data

(63) Continuation-in-part of application No. 08/984,380, filed on Dec. 3, 1997, now abandoned, which is a continuation-in-part of application No. 08/857,724, filed on May 16, 1997, now abandoned.

(51) Int. Cl.⁷ .............................................. A61B 19/00
(52) U.S. Cl. ...................................... 128/849; 128/850
(58) Field of Search ................................. 128/849–856

(56) References Cited

U.S. PATENT DOCUMENTS

| | | | |
|---|---|---|---|
| 1,852,040 A | 4/1932 | Blank | |
| 2,725,322 A | 11/1955 | Muttera, Jr. | 154/53.5 |
| 3,018,881 A | 1/1962 | Wall | 206/56 |

(List continued on next page.)

FOREIGN PATENT DOCUMENTS

| | | |
|---|---|---|
| DE | 38 09 539 A1 | 10/1989 |
| EP | 0 081 987 A1 | 6/1983 |
| EP | 0 091 800 B2 | 10/1983 |
| EP | 0 120 840 | 10/1984 |
| EP | 0 520 330 B1 | 12/1992 |
| EP | 0 549 948 A1 | 7/1993 |
| EP | 0 568 401 A1 | 11/1993 |
| EP | 0 597 636 A1 | 5/1994 |
| EP | 0 640 352 A1 | 3/1995 |
| GB | 1132770 | 11/1968 |
| GB | 2 131 299 A | 6/1984 |
| GB | 2157955 | 11/1985 |
| WO | WO 84/01285 | 4/1984 |
| WO | WO 88/08690 | 11/1988 |
| WO | WO 89/01345 | 2/1989 |
| WO | WO 90/00066 | 1/1990 |
| WO | WO 91/14462 | 10/1991 |
| WO | WO 93/02717 | 2/1993 |
| WO | WO 93/17633 | 9/1993 |
| WO | WO 94/24977 | 11/1994 |
| WO | WO 97/42904 | 11/1997 |

OTHER PUBLICATIONS

ASTM C 4032–92 Standard Test Method for Stiffness of Fabric by the Circular Bend Procedure; p. 277–281.

*Primary Examiner*—Michael A. Brown
(74) *Attorney, Agent, or Firm*—Nancy M. Lambert

(57) ABSTRACT

A surgical incise drape comprising a flexible film having a leading edge and a trailing edge, and a film handle applied at the leading edge of the flexible film. A liner substantially covers the major portion of the flexible film, which is coated with an adhesive. The liner may include a liner handle at the leading edge, and one of the liner handle and film handle are of a size for wrapping about at least a portion of the drape when the drape is in a folded configuration. A tensioning strip may be applied to the liner at a position away from the leading edge of the liner to hold at least a portion of the flexible film lying between the film handle and the tensioning strip in a wrinkle-free state when the liner is being removed from the major portion of the flexible film. Further, the liner may be stiff relative to the flexible film such that the liner and the film handle hold the flexible film in a wrinkle-free state when the liner is being removed from the major portion of the flexible film. Methods for using these surgical incise drapes, tear lines, and connecting or reinforcement strips are also described.

31 Claims, 9 Drawing Sheets

U.S. PATENT DOCUMENTS

| | | | | |
|---|---|---|---|---|
| 3,878,843 | A | 4/1975 | Morgan | 128/132 |
| 3,916,887 | A | 11/1975 | Kelly | 128/132 |
| 3,930,502 | A | 1/1976 | Tritsch | 128/287 |
| 4,310,509 | A | 1/1982 | Berglund et al. | 424/28 |
| 4,323,557 | A | 4/1982 | Rosso et al. | 424/28 |
| 4,372,303 | A | 2/1983 | Grossman et al. | 128/132 |
| 4,374,520 | A | 2/1983 | Grossman et al. | 128/132 |
| 4,452,845 | A | 6/1984 | Lloyd et al. | 428/220 |
| 4,513,739 | A | 4/1985 | Johns | 128/156 |
| RE31,886 | E | 5/1985 | Hodgson | 428/40 |
| RE31,887 | E | 5/1985 | Hodgson | 428/355 |
| 4,524,767 | A | 6/1985 | Glassman | 128/132 |
| 4,545,371 | A | 10/1985 | Grossman et al. | 128/132 |
| 4,598,004 | A | 7/1986 | Heinecke | 428/40 |
| 4,614,183 | A | 9/1986 | McCracken et al. | 128/132 |
| 4,701,509 | A | 10/1987 | Sun et al. | 526/264 |
| 4,711,236 | A | 12/1987 | Glassman | 128/132 |
| 4,732,808 | A | 3/1988 | Krampe et al. | 428/355 |
| 4,744,355 | A | 5/1988 | Faasse, Jr. | 128/156 |
| 4,753,232 | A | 6/1988 | Ward | 128/156 |
| 4,781,293 | A | 11/1988 | Johns | 206/441 |
| 4,798,201 | A | 1/1989 | Rawlings et al. | 128/156 |
| 4,832,008 | A | 5/1989 | Gilman | 128/155 |
| 4,846,164 | A | 7/1989 | Martz | 128/155 |
| 4,884,563 | A | 12/1989 | Sessions | 128/155 |
| 4,906,240 | A | 3/1990 | Reed et al. | 604/307 |
| 4,914,173 | A | 4/1990 | Ansell | 528/49 |
| 4,931,282 | A | 6/1990 | Asmus et al. | 424/448 |
| 4,942,029 | A | 7/1990 | Scheps | 424/78 |
| RE33,353 | E | 9/1990 | Heinecke | 428/40 |
| 5,012,801 | A | 5/1991 | Feret | 128/155 |
| 5,017,625 | A | 5/1991 | Ansell | 521/159 |
| 5,061,258 | A | 10/1991 | Martz | 604/307 |
| 5,074,293 | A | 12/1991 | Lott et al. | 128/155 |
| 5,092,323 | A | 3/1992 | Riedel et al. | 602/54 |
| 5,151,314 | A | 9/1992 | Brown | 428/198 |
| 5,153,040 | A | 10/1992 | Faasse, Jr. | 428/40 |
| 5,156,911 | A | 10/1992 | Stewart | 428/355 |
| 5,183,664 | A | 2/1993 | Ansell | 424/445 |
| 5,188,124 | A | 2/1993 | Feret | 128/889 |
| 5,197,493 | A | 3/1993 | Grier-Idris | 128/853 |
| 5,204,110 | A | 4/1993 | Cartmell et al. | 424/443 |
| 5,290,615 | A | 3/1994 | Tushaus et al. | 428/40 |
| 5,387,466 | A | 2/1995 | Therriault et al. | 428/355 |
| 5,437,622 | A | 8/1995 | Carion | 602/57 |
| 5,480,377 | A | 1/1996 | Cartmell et al. | 602/48 |
| 5,593,395 | A | 1/1997 | Martz | 604/304 |
| 5,633,070 | A | 5/1997 | Murayama et al. | 428/194 |
| 5,722,943 | A | 3/1998 | Sessions | 602/57 |
| 5,979,450 | A * | 11/1999 | Baker | 128/849 |
| 5,985,395 | A | 11/1999 | Comstock et al. | 428/40.1 |

\* cited by examiner

SURGICAL INCISE DRAPE

RELATED APPLICATIONS

This application is a continuation-in-part of U.S. patent application Ser. No. 08/984,380, filed Dec. 3, 1997 now abandoned, which is a continuation-in-part of U.S. patent application Ser. No. 08/857,724, filed May 16, 1997 now abandoned.

FIELD OF THE INVENTION

The present invention relates to the field of surgical incise drapes. More particularly, the present invention pertains to surgical incise drapes having liners that provide tension for these drapes during application.

BACKGROUND OF THE INVENTION

Many of today's surgical procedures involve the use of a surgical incise drape. The incise material is usually a clear polymeric film with an adhesive on one side that is covered with a release liner. Two suppliers of incise materials are Minnesota Mining and Manufacturing Company, St. Paul, Minn., and T. J. Smith and Nephew Ltd. Examples of incise material can be found in U.S. Pat. Nos. 4,310,509; 4,323,557; 4,452,845; Re. 31,886; and Re. 31,887.

Typically, incise material is used in connection with towels or surgical drapes to maintain the surgical area as clean and sterile as possible to help reduce the risk of infection. Once the surgical area of the patient has been cleaned and treated with an antimicrobial, the surgical site is squared-off by the use of sterile towels and a surgical drape that has a fenestration (i.e., a specifically designed shape and opening formed therein) of a size that is larger than the expected size of the incision. An incise material is then used to cover all or a portion of the patient's skin left exposed by the towels or the fenestration in the surgical drape or main sheet.

One purpose for using the incise material is to help reduce the migration of germs and bacteria into the incision site. This reduction is needed, because despite the cleansing of the skin, the pores still contain additional germs and bacteria, which can migrate to the surface as the skin is moved and worked during the course of the surgical procedure. By covering the skin with incise material, it has been found that a lower incidence of surgical site contamination occurs.

Common practice is to take the sterile incise drape out of a disposable, protective bag (e.g., made from polyethylene), further remove any other protective coverings, and deliver it to the sterile field in an aseptic manner. For example, the protective coverings may be materials such as paper wraps for wrapping around the drape to allow the drape to be inserted into the disposable protective bag without tearing or wrinkling the drape in the packaging process. The use of multiple protective coverings result in added waste in the surgical area.

The surgical incise drape typically comes in sizes as small as 13×18 cm (5×7 inches) but are usually 40×30 cm (16×12 inches) up through 90×120 cm (36×48 inches) and larger. Conventional surgical incise drapes usually consist of an adhesive coated incise material covered by a one-piece coated paper release liner with equal dimensions as the film so that the adhesive is protected.

Typical practice is for two people to stand on opposite sides of the operating table, each within the sterile field with sterile gloved hands. One person grips a handle portion of the drape (a 10 to 15 cm film margin free of adhesive) while the other person takes the paper liner and pulls it way from the underside exposing the adhesive. The drape is then applied to the patient at the surgical site and subsequently smoothed out and pressed onto the patient with a sterile towel. With larger drapes, this might require three or more people.

Current incise drapes are usually large and cumbersome to apply to the patient without wrinkles and without the drape sticking to itself in the process. As described above, drape application usually requires two or three people, creating a drain on operating room personnel and contributing to rising hospital costs. Applying conventional incise drapes can be a frustrating experience, even for those skilled in the art of applying these drapes. The drape is flimsy (so as to be very conformable to the contours of the skin) with an aggressive pressure sensitive adhesive for adhesion to the skin. These two characteristics, when combined with the large size of many incise drapes, frequently results in the application of a wrinkled drape.

For proper functioning of a surgical incise drape, it is important that the incise drape be wrinkle-free after it is applied, especially directly at the incision point in order for the surgeon to be able to make a clean surgical incision. Wrinkles in the drape make it difficult for the surgeon to see through to the skin (translucency and visibility are important). Furthermore, if the incise drape includes wrinkles, the incise drape may not prevent bacteria on the skin from getting into the wound. Maintaining a sterile surface at the point of incision helps prevent surgical wound infections. Further, it is important that the incise drape be easily applied with as few steps as possible, and that waste resulting from use of the incise drape be minimized.

SUMMARY OF THE INVENTION

This invention provides a surgical incise drape that can be effectively and efficiently applied to a patient in wrinkle-free form so as to minimize the chance of infection, improve the visibility through the film as the drape is applied to a patient, and reduce the amount of waste resulting from the use of the drape.

A surgical incise drape in accordance with the present invention includes a flexible film having a major portion coated with an adhesive. The flexible film has a leading edge and a trailing edge. The drape further includes a film handle at the leading edge of the flexible film with the film handle being stiffer than the flexible film. Yet further, the drape includes a liner having a leading edge and a trailing edge corresponding to the leading edge and trailing edge of the flexible film. The liner includes a liner handle at the leading edge and the liner substantially covers the major portion of the flexible film coated with the adhesive. Either the liner handle or film handle is of a size for wrapping about at least a portion of the drape when the drape is in a folded configuration.

In one embodiment of the drape, either the liner handle or film handle is of a size for wrapping about the entire periphery of the drape when the drape is in the folded configuration. In another embodiment of the drape, the drape further includes a closure element attached to the liner handle or the film handle and extending for attachment to another portion of the drape when the drape is in the folded configuration. In yet another embodiment of the drape, the drape in the folded configuration is flattened such that the drape includes creases at respective opposing regions thereof.

In another embodiment of the drape, the liner is relatively stiff compared to the flexible film such that the liner and the film handle hold the flexible film in a wrinkle-free state when the liner is being removed from the major portion of the flexible film. For example, the liner may be a polyolefin liner having a thickness of at least about 50 microns and preferably at least about 75 microns. Further, for example, the liner may be a polyethylene liner, such as a medium density or high density polyethylene liner.

In another embodiment of the drape, the liner includes at least one tensioning strip at a position away from the leading edge of the liner so as to hold at least a portion of the flexible film lying between the film handle and the one or more tensioning strips in a wrinkle-free state when the liner is being removed from the major portion of the flexible film. For example, a tensioning strip may be at the trailing edge of the liner and/or at any position between the leading edge and trailing edge of the liner.

In another embodiment of the drape, the adhesive coating the major portion of the flexible film includes a first adhesive region proximate the leading edge of the flexible film and a second adhesive region at or near the trailing edge of the flexible film. A greater force is required to remove the liner from the second adhesive region relative to removing the liner from the first adhesive region.

Another surgical incise drape in accordance with the present invention includes a flexible film having a major portion coated with an adhesive. The flexible film has a leading edge and a trailing edge. A film handle is included at the leading edge of the flexible film. The drape further includes a liner having a leading edge and a trailing edge corresponding to the leading edge and trailing edge of the flexible film. The liner substantially covers the major portion of the flexible film coated with the adhesive. Further, the liner includes at least one tensioning strip at a position away from the leading edge of the liner so as to hold at least a portion of the flexible film lying between the film handle and the tensioning strip in a wrinkle-free state when the liner is being removed from the major portion of the flexible film. The tensioning strip is stiffer than the liner.

A method for use with a surgical incise drape in accordance with the present invention is also described. The method includes providing a substantially flat surgical incise drape. The drape includes a flexible film having a major portion coated with an adhesive. The flexible film has a leading edge and a trailing edge with a film handle applied at the leading edge of the flexible film. Further, the drape includes a liner having a leading edge and a trailing edge corresponding to the leading edge and trailing edge of the flexible film. The liner substantially covers the major portion of the flexible film coated with the adhesive. The method further includes folding the drape from the trailing edge to the leading edge and then wrapping one of the film handle and the liner handle about at least a portion of the folded drape.

Methods for using these surgical incise drapes are also described. Generally, the methods include providing a drape, grasping the film handle of the drape, pulling upon the liner to remove at least a portion of the liner exposing at least a portion of the adhesive coating the major portion of the flexible film, holding the surgical incise drape in a position such that at least a portion of the adhesive is contacting the patient, and then removing portions of the liner remaining.

In yet another aspect of the invention, the surgical drape generally comprises an elastomeric film having a major portion coated with an adhesive. The flexible film has a leading edge, a trailing edge and opposite side edges. A handle is provided at the leading edge of the flexible film. The handle is formed of sheet material that is stiffer than the elastomeric film. A tear line is provided in the elastomeric film extending generally adjacent, and generally parallel with, the leading edge for facilitating propagating tearing of the film along the tear line to separate the handle from the elastomeric film. The tear line has opposite ends spaced from the opposite side edges of the film.

Preferably, the tear line comprises a line of perforations, and the opposite ends of the tear line are spaced from the opposite side edges of the elastomeric film by at least 0.5 cm. More preferably, the opposite ends of the tear line are spaced from the opposite side edges of the elastomeric film by at least 1 cm, and most preferably 2 cm or even 2.5 cm.

Also, preferably, the elastomeric film has a thickness no greater than 75 microns, most preferably no greater than 52 microns.

Alternatively, the tear line comprises the elastomeric film being scored or otherwise made thinner along the tear line than along the elastomeric film generally to facilitate propagating tearing along the tear line.

In yet another aspect of the invention, the surgical incise drape generally comprises an elastomeric film having a major portion coated with an adhesive. The flexible film having a leading edge, a trailing edge and opposite side edges. A handle is provided adjacent the leading edge of the flexible film, and an elongate strip connects the film and handle along the leading edge of the film. The strip has more tear resistance than the elastomeric film. The strip has one or more tear lines for facilitating propagating tearing of the strip along the tear line to separate the handle from the elastomeric film.

Preferably, the tear line comprises a line of perforations. Also, preferably, the handle is formed of sheet material that is stiffer than the elastomeric film.

The elongate strip preferably comprises reinforcement tape that is more resistant to tearing than the film or handle other than along the tear line. Preferably, the reinforcement tape is a film tape having one surface coated with an adhesive, most preferably a pressure sensitive adhesive. For example, the film tape may comprise a low-density polyethylene film tape, and the adhesive comprises an acrylate adhesive.

DETAILED DESCRIPTION OF PREFERRED EMBODIMENTS

The present invention provides surgical incise drapes and methods of applying these drapes effectively and efficiently to a patient in wrinkle-free form so as to minimize the chance of infection and to improve visibility during application of the incise drape to the patient. As previously described, it is important that the incise drape be wrinkle-free after it is applied, especially directly at the incision point in order for the surgeon to be able to make a clean surgical incision and reduce the chance of microbial contamination. Further, it is important that the incise drape be easily applied with as few steps as possible and with minimal waste products resulting from such application.

Figure 1A:
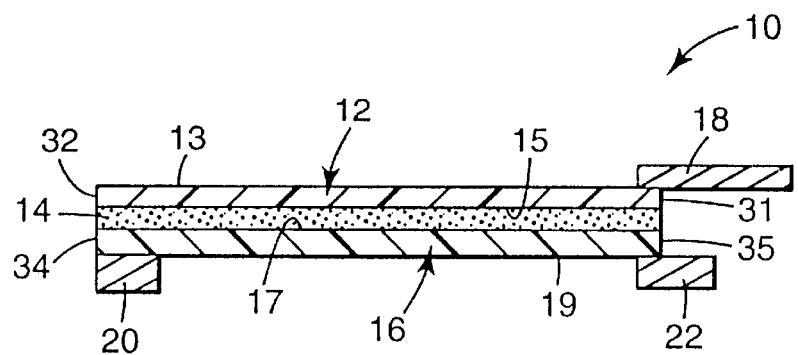
FIGS. 1A–1E are sectional views of a surgical incise drape in accordance with the present invention at various points in the method of applying the surgical incise drape to a patient.
Figure 1B:
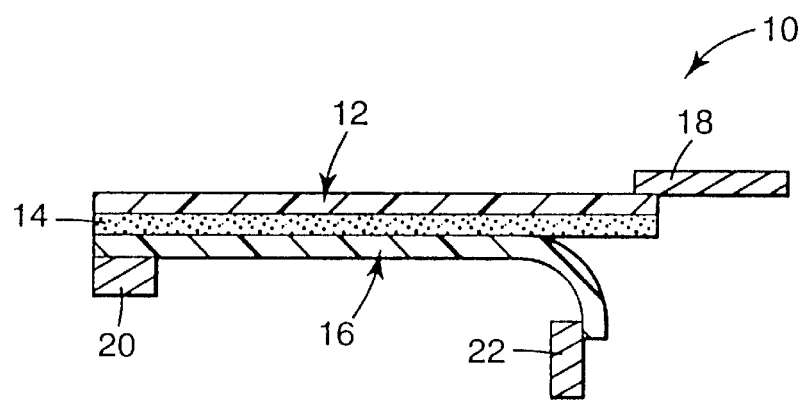
Figure 1C:
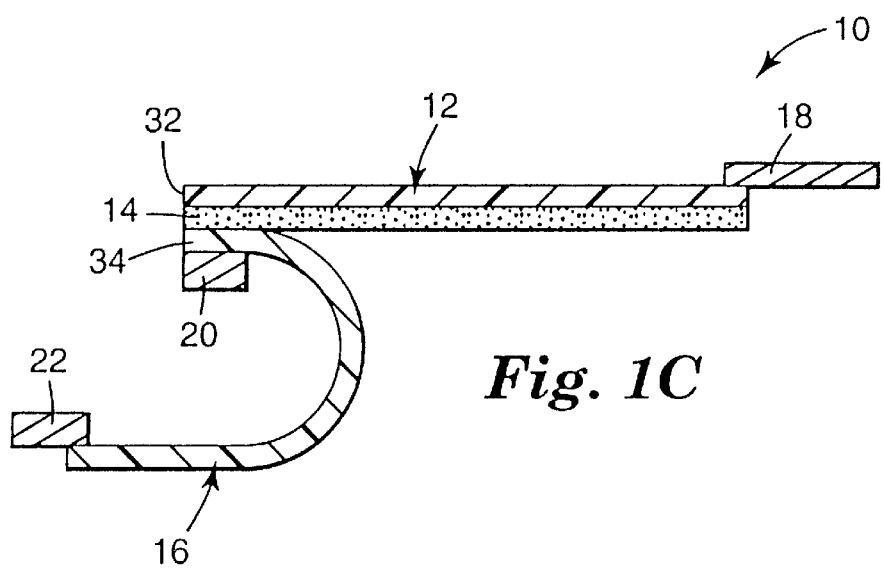
Figure 1D:
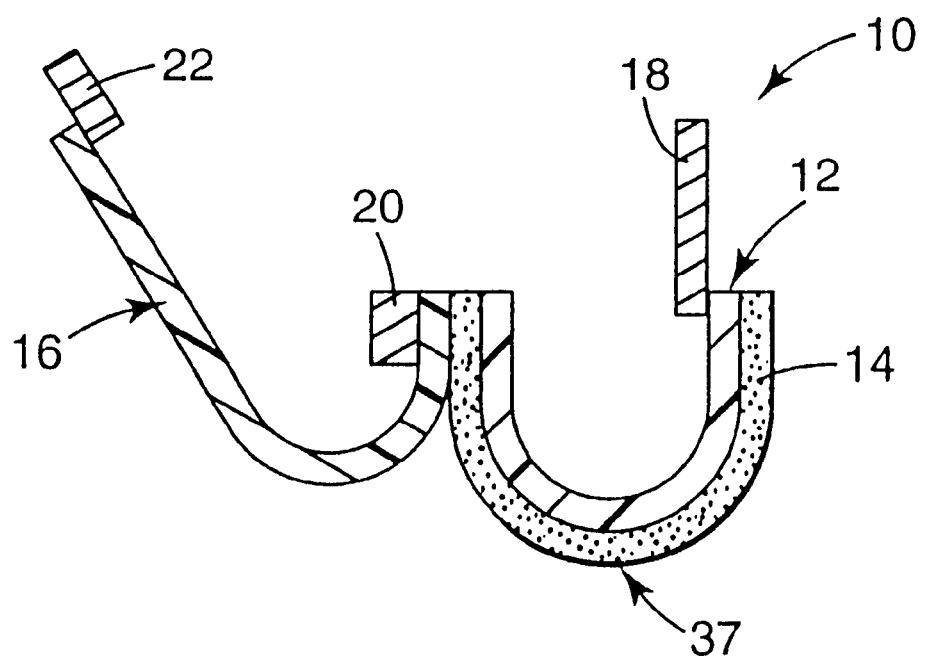
Figure 1E:
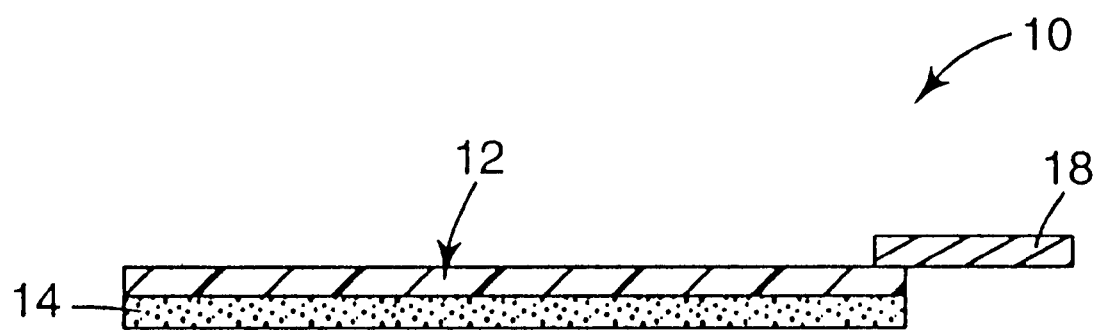
Figure 2:
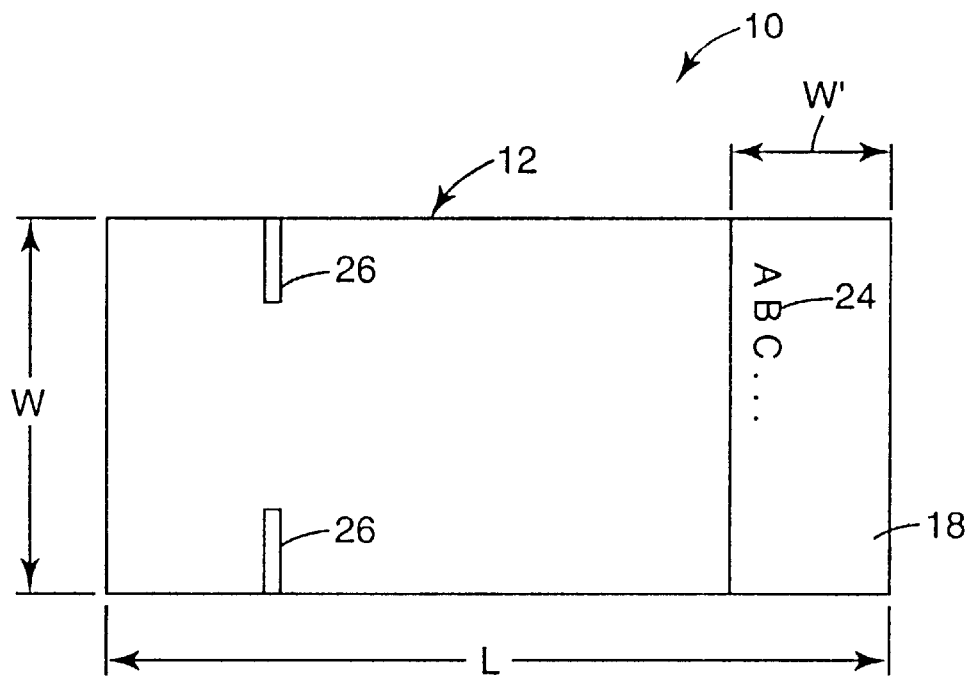
FIG. 2 is a top film-side plan view of the surgical incise drape shown in FIG. 1.
Figure 3:
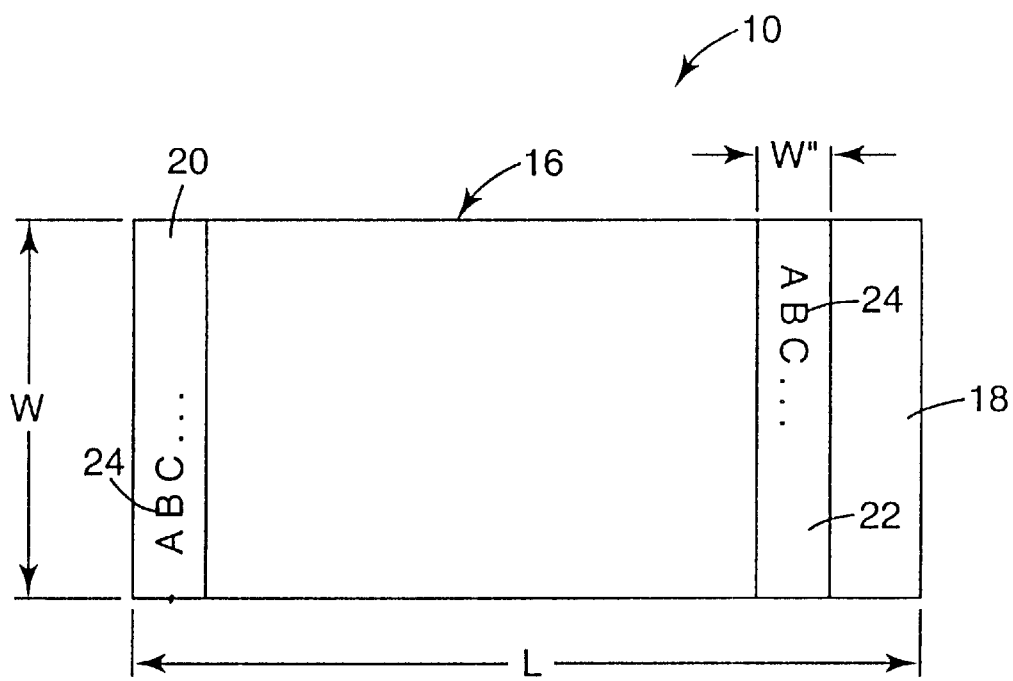
FIG. 3 is a bottom liner-side plan view of the surgical incise drape shown in FIG. 1.

With reference to FIGS. 1–3, a surgical incise drape 10 in accordance with the present invention is described. Further, with particular reference to FIGS. 1A–1E, a method of applying the surgical incise drape 10 to a patient is described. The remaining FIGS. 4–10 show alternative drape configurations for such a surgical incise drape.

As shown in FIGS. 1–3, the surgical incise drape 10 is generally of a rectangular configuration, however, any size or shape may be suitable as long as the surgical incise drape provides the benefits as further described in detail below. For example, the drape 10 may have a width (W) of about 10 cm to about 150 cm and a length (L) of about 10 cm to about 150 cm. The surgical incise drape 10 includes film 12, such as a transparent flexible film. The flexible film 12 includes an upper surface 13 and a lower surface 15 extending from a leading edge 31 of the flexible film 12 to a trailing edge 32 of the flexible film 12.

The flexible film 12 of the incise drape is formed from a transparent or translucent polymeric material. The material preferably allows for moisture evaporation through the film during prolonged surgeries. Suitable materials include polyolefins, such as low density polyethylene and particularly metallocene polyethylenes such as Engage™ polyethylenes commercially available from Dow Chemical, polyurethanes such as polyester or polyether polyurethanes (e.g., "Estane™ thermoplastic polyurethane," commercially available from B. F. Goodrich, Cleveland Ohio), polyesters such as polyether polyester (e.g., "Hytrel™ polyester elastomer," commercially available from Du Pont Co., Wilmington, Del.), and polyamides such as polyether polyamides (e.g., "Pebax™ Resins" commercially available from ELF Atochem, North America, Inc., Philadelphia, Pa.).

Furthermore, the film 12 is flexible, and preferably somewhat elastomeric, to improve conformability when applied to a patient. For these reasons, the preferred films are polyurethanes, polyether polyesters, and polyether polyamides. The film 12 will typically have a thickness of less than about 200 microns, preferably between about 6 microns to about 130 microns, and most preferably between about 13 microns and about 52 microns.

At least a major portion of the lower surface 15 of the flexible film 12 is coated with a pressure sensitive adhesive 14. Although FIG. 1 shows that the entire length of the flexible film 12 is coated with the adhesive 14, any major portion may be coated that allows the surgical incise drape to serve its useful function, e.g., the adhesive need not coat the entire width or length of the drape. For example, non-coated portions may be included at any of the edges of the flexible film to assist in removal of the drape from the patient or to assist in attachment of a handle to the film.

The adhesive 14 coating the flexible film 12 is preferably a tacky pressure sensitive adhesive at body temperature that will adhere aggressively to the skin. Uniform attachment to the skin surface helps maintain a sterile surgical field. Aggressive adhesives are preferred due to the stress the film 12 is under during surgery as a result of the retraction of the wound, the warm moist environment, and the abrasion the film 12 may encounter as the surgeon's hands and instruments move in and out of the wound.

Suitable adhesives include acrylic adhesives, adhesives based on Kraton™ or Kraton™ polymers (Shell Chemical Company, Houston, Tex.), rubber based adhesives such as those based on natural rubber, polyisobutylene, butylene rubbers and the like, polyurethane type adhesives, and polyvinylethyl ether and copolymers or blends thereof. Preferably, the adhesive also contains an antimicrobial such as iodine, triiodide complexes, lactam-triiodide complexes such as povidoneiodine, chlorhexidine salts such as chlorhexidine gluconate and chlorhexidine acetate, polymeric biguanides, hexachlorophene, parachlorometaxylenol (PCMX), triclosan, phenols, fatty acid monoesters such as Lauricidin (glycerol monolaurate), quaternary surfactants, silver, and silver salts such as silver chloride, silver oxide and silver, hydrogen peroxide and the like.

The adhesive 14 is preferably one of those described in U.S. Pat. Nos. 4,323,557; 4,931,282; 4,701,509; 4,732,808; 5,156,911; 5,017,625; and 5,204,110. Further, the adhesive 14 may be a continuous coating or may be a pattern coated as described in U.S. Pat. Nos. 4,798,201 and 5,290,615. These adhesive types may also include various chemical modifiers, e.g., tackifiers, crosslinkers, stabilizers, initiators, etc. to improve physical properties such as stability, viscosity, adhesion and the like.

The pressure sensitive adhesive 14 is covered by a release liner 16. The release liner 16 includes an upper surface 17 in contact with the pressure sensitive adhesive 14. The upper surface 17 and a lower surface 19 extend between a leading edge 35 and a trailing edge 34 of the liner 16. The leading edge 35 of the liner 16 generally corresponds with the leading edge 31 of the film 12 and the trailing edge 34 of the liner 16 generally corresponds to the trailing edge 32 of the film 12. Although edges 35, 31, as well as edges 34, 32, need not overlap, i.e., the liner 16 may be smaller or larger than film 12, the liner 16 should fully cover the adhesive 14.

The release liner 16 could be made of a variety of materials such as paper, plastic coated paper, plastic film, woven, non-woven, or knit textiles, as well as film textile laminates. The liner 16 may be hydrophilic to allow fluid absorbency or may be hydrophobic without absorbency. Preferred release liner materials include clear polymeric liners that allow the clinician to see through to the patient and thus accurately place the film 12 during application of the film 12 to a patient as described further below. Preferred clear polymeric liners include polyolefins such as polyethylene and polypropylene, or polyester liners, as well as laminates such as polyolefin coated polyester. For products intended for gamma sterilization, use of a paper, polyethylene, polyester, or polyethylene coated polyester liner is preferred.

One method manufacturing the incise drape involves coating an adhesive solvent solution onto the liner, removing the solvent in an oven, and subsequently laminating this adhesive-coated liner to the film backing. Since the solvent is removed typically at elevated temperature in an oven, certain low melting thermoplastic polymeric liners such as those made of low or medium density polyethylene may be adversely effected. And liners incorporating a higher melting thermoplastic polymer such as a polyester layer, which are able to withstand the elevated temperature during drying, are not very flexible and can be quite noisy during application. A preferred approach is to form film liners by laminating polymers with high melting points and polymers with low melting points.

Desirable high melting point polymers for the preferred laminated film are characterized by having a melt temperature in excess of about 175° C. and preferably in excess of about 190° C. (as listed in Modern Plastics Encyclopedia Vol. 66 no. 11, 1989, McGraw Hill). Polymers useful for this layer include but are not limited to polyester (e.g. polyethylene terephthalate, polybutylene terephthalate etc.), polyamides (e.g. nylon 6,6; nylon 6), cellulose acetate and the like. The high melting point polymer layer should generally be present in the laminate in a total thickness (i.e., the sum total of all layers) of at least about 6 microns, preferably at least 12 microns and most preferably at least about 25 microns.

Desirable low melting point polymers for the preferred laminated film are characterized by having a melt temperature below about 175° C. and preferably below about 150° C.). Polymers useful for this layer include but are not limited to polyolefins (e.g., polyethylene, polypropylene, polybutylene, ethylene/vinyl acetate, ethylene methylacrylate and the like). The low melting point polymer layer should generally be present in the laminate in a total thickness (i.e., the sum total of all layers) of at least about 12 microns, preferably at least 25 microns and most preferably at least about 50 microns.

The preferred laminated film liner may be formed of two or more thermoplastic polymer layers, although one of the layers could be a thermoset if desired. For example, a high melting point polymer layer may be laminated on one or both sides by a low melting point polymer. In this manner, the high melting point polymer layer is able to support the stresses imparted in the drying oven while the low melting point polymer layer provides flexibility. In addition to the polymer layers, a low adhesion backsize (LAB) coating can be applied to one or both major surfaces of the multi-layered laminated film.

These laminated films may be formed by laminating premade films formed by any suitable method such as cast or blown extrusion. Alternatively, the laminates may be formed by coextrusion or extrusion lamination techniques.

A release coating of silicone, fluoro-chemical containing, long chain alkyl containing material, or other low surface energy coating, is applied to the upper surface 17 of the liner 16. This coating allows the liner 16 to be peeled away from the adhesive 14 with a force of less than about 120 g/cm, preferably less than 80 g/cm, more preferably less than 40 g/cm, and most preferably less than 25 g/cm when measured in a 180° peel at a speed of 225 cm per minute, at 25° C. and at 50 percent relative humidity. A preferred release coating is "GE Silicone SS4331 Low Temperature, Fast Cure Paper Premium Release Coating" available from General Electric Company, Waterford, N.Y. The amount of the release coating will vary depending on the level of adhesion and coating thickness of the adhesive 14. A preferred polyethylene release liner is available from Rexam Release (Eagan, Minn.) as Grade 10521 54 mil NT LDP A16/000. A preferred polypropylene liner is also available from Rexam Release as Grade 15529D 2 mil CL BOP Exp/000.

The flexible film 12 is provided with a film handle 18 at the leading edge 31 of the film 12. The film handle 18 is preferably formed of a relatively stiff material as compared to the flexible film 12. When tested according to the ASTM test method D4032-92 (Standard Test Method for Stiffness of Fabric by the Circular Bend Procedure), the flexible film has an average stiffness of generally less than about 1.1N and preferably less than about 0.5N. The film handle 18 generally has a stiffness of greater than about 2N, preferably greater than about 4N, more preferably greater than about 8N, and most preferably greater than about 20N.

As shown in FIG. 1A, the film handle 18 is attached to the upper surface 13 of the flexible film 12 at the leading edge 31 and is attached along the entire width (W) of the film 12 as shown in FIGS. 2 and 3. Alternatively, the film handle can be attached to the underside of flexible film utilizing the adhesive coating the flexible film, such as shown and described below with reference to FIG. 4D. Further, alternatively, various adhesives may be used for attachment of the film handle to the flexible film.

The film handle 18 may be formed of paper, paper board, plastic or plastic coated paper. Preferred papers have basis weights of about 80 $g/m^2$ to about 400 $g/m^2$, more preferably about 100 $g/m^2$ to about 300 $g/m^2$, and most preferably about 150 $g/m^2$ to about 225 $g/m^2$. Plastic films are preferably polyester or high density polyethylene having a thickness of about 52 microns to about 250 microns, preferably about 75 microns to about 225 microns, and most preferably about 100 microns to about 200 microns.

The film handle 18 may be applied at the leading edge 31 of the film 12 in one of various ways, including use of a releasable adhesive as further described below. For example, the handle 18 may be applied to the film 12 by thermal bonding; ultrasonic welding; or with use of a pressure sensitive adhesive, such as double coated pressure sensitive adhesive, pressure sensitive adhesive tape, curable pressure sensitive adhesive, as well as solvent or aqueous based adhesives, including the pressure sensitive adhesive 14 used to ensure good skin adhesion.

The release liner 16 is provided with a liner handle 22 at the leading edge 35 of the liner 16. The handle 22 is preferably formed of a relatively stiff material as compared to the flexible film 12. The preferred stiffness range of handle 22 is substantially the same as that for handle 18. However, it is not necessary for handle 22 to be stiffer than the liner 16 to obtain benefits from use of the present invention. As shown in FIG. 1A, the handle 22 is attached to the lower surface 19 of the liner 16 at the leading edge 35 and preferably is attached along the entire width (W) of the liner 16 as shown in FIG. 3.

The liner handle 22 may be formed of materials similar or identical to the material of handles 18 or it may be formed from the same material as the liner 16, including multiple layers of liner 16 such as may be formed by folding a protruding edge 35 of liner 16 over upon itself. The liner handle 22 may be applied to the leading edge 35 of the liner 16 in one of various ways, including being an integral portion of the liner 16 itself that extends beyond the adhesive 14 coating the film 12. For example, the liner handle 22 may be applied to the liner 16 by methods and materials similar to or identical to those used for applying handle 18 to film 12.

The handles 18 and 22 are preferably at least about 2.5 cm in width (W', W"), more preferably at least about 3.5 cm, and most preferably about 5 cm or more to allow for ease in grasping by a gloved applier. At least one of the handles is preferably of a size suitable for use in protecting the drape after rolling or folding of the drape as further described below with reference to the alternative drape configurations of FIGS. 8A–8C. As shown in FIG. 1A, the film handle 18 is longer than the liner handle 22 to serve this function. However, it is readily apparent that the liner handle could be longer than the film handle to serve the same function.

FIGS. 4A–4E are detailed views of film handle and liner handle portions of alternative surgical incise drape configurations. As shown in the alternative drape configuration 40 of FIG. 4A, both a film handle 47 and liner handle 45 are attached to the respective leading edges of flexible film 42 and release liner 46 by pressure sensitive adhesives. The liner handle 45 is attached to the release liner 46 by pressure sensitive adhesive 49. The film handle 47 is attached to the flexible film 42 coated with pressure sensitive adhesive 44 by pressure sensitive adhesive 48. The pressure sensitive adhesive 48 coated on either the leading edge of flexible film 42 or the handle itself allows all or part of the handle 47 to be removed after application of the film 42 to a patient. The adhesive 49 coated on the leading edge of the release liner 46 allows the liner handle 45 to be removed such that the adhesive 49 can be used to position the liner 46, once removed completely from film 42, at a different location to function as an additional drape as further described below.

Figure 4A:
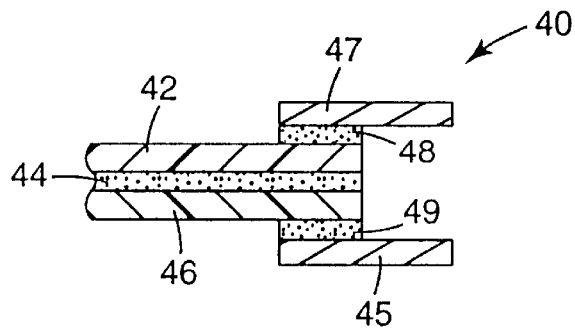
FIGS. 4A–4E are sectional views of the film handle and the liner handle portions of alternative surgical incise drape configurations.
Figure 4B:
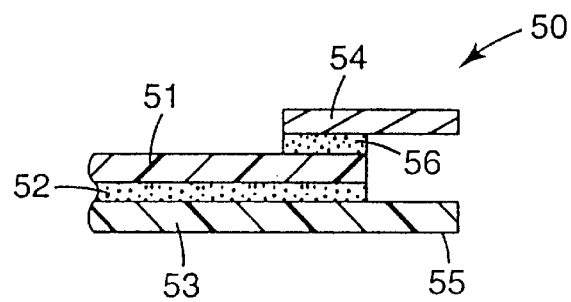

As shown in the alternative drape configuration 50 of FIG. 4B, the film handle 54 is releasably attached to flexible film 51 by pressure sensitive adhesive 56 so that the handle 54 can be removed after application of the flexible film 51 to a patient. Preferably, adhesive 56 is removed along with handle 54. This may be accomplished by using an adhesive 56 that does not permanently bond to film 51 (e.g., coating film 51 with a low surface energy material at least at the edge where adhesive 56 is applied). Such low surface energy materials are commonly referred to as low adhesion backsizes and may be polysiloxine, fluoro-chemical or hydrocarbon based materials, as well as blends or mixtures thereof.

The release liner 53 that is applied to the pressure sensitive adhesive 52 coated on the film 51 is provided with a liner handle 55 that is integral with the release liner 53 and extends beyond the adhesive 52 coated on the surface of the flexible film 51. The liner handle 55 can be grasped for application of the flexible film 51 as generally described below.

Figure 4C:
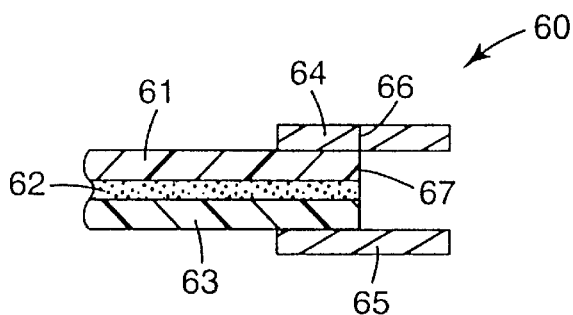

As shown in the alternative drape configuration 60 of FIG. 4C, the film handle 64 is removably attached to the flexible film 61 using perforation 66. As shown, the handle 64 is permanently attached to the film 61 at the leading edge 67 of the film 61 and a perforation 66 is provided such that a portion of the handle extending beyond the leading edge 67 of the film 61 can be removed after application to a patient. In the drape configuration 60, the liner handle 65 is permanently attached to the release liner 63 that covers adhesive 62 coated on film 61 by any known bonding technique such as, for example, thermal bonding, ultrasonic welding, etc.

Figure 4D:
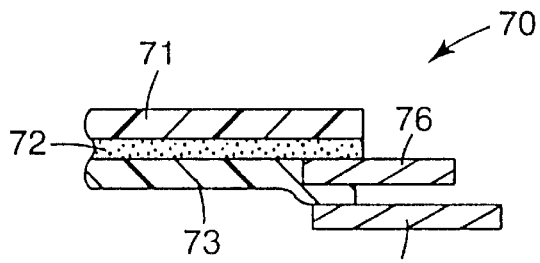
Figure 4E:
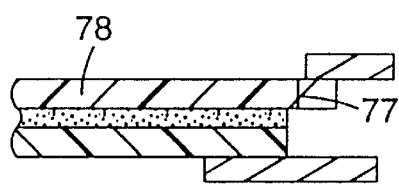

Alternatively, as shown in FIG. 4E, a perforation or notch 77 may be made in the flexible film 78. Preferably, this perforation is placed in a nonadhesive coated section of the film (as shown), which facilitates tearing to remove the film handle.

Also, as shown in FIG. 4C, liner handle 65 extends further from the leading edge 67 than film handle 64, i.e., liner handle 65 is longer than film handle 64. The extended length of liner handle 65 facilitates locating the handles for application of the drape. Alternatively, the length of film handle 64 may extend beyond handle 65, one handle may be of a distinct color, pattern, or have some other feature distinguishing characteristic that would differentiate one handle from the other. Further, the extended length of liner handle 65 is preferably suitable for use in protecting the drape after rolling or folding of the drape as further described below with reference to FIGS. 8A–8C.

As shown in the alternative drape configuration 70 of FIG. 4D, the film handle 76 is releasably attached to flexible film 71 by pressure sensitive adhesive 72 at the underside of the film 71 such that the handle 76 can be removed after application of the flexible film 71 to a patient. The release liner 73 that is applied to the pressure sensitive adhesive 72 coated on the film 71 is provided with a liner handle 75 that extends past the handle 76 and is applied in any manner as previously described herein.

Further with reference to FIG. 1, the release liner 16 of surgical incise drape 10 is also provided with a tensioning strip 20 at the trailing edge 34 of the liner 16. The tensioning strip 20 is formed of a relatively stiff material as compared to the flexible film 12. The tensioning strip when tested according to ASTM D4032-92 has a stiffness of generally greater than about 2N, preferably greater than about 4N, more preferably greater than about 8N, and most preferably greater than about 20N. As shown in FIG. 1A, the tensioning strip 20 is attached to the lower surface 19 of the liner 16 at the trailing edge 34 and preferably is attached along the entire width (W) of the liner 16 as shown in FIG. 3.

The use of a tensioning strip is particularly beneficial when the liner is relatively flexible, i.e., the stiffness of the liner is less than about 20N, and especially beneficial if the stiffness of the liner is less than about 10N. However, as described with reference to FIG. 7, the tensioning strip is optionally included in accordance with the present invention. In particular, a tensioning strip may not be necessary when the liner is stiff enough to provide adequate tensioning of the flexible film during application of the film to a patient. However, one or more tensioning strips may be used independent of liner stiffness.

The tensioning strip 20 may be formed of materials similar to or identical to those for forming handles 18 and 22. The tensioning strip 20 is preferably 8 mm wide, more preferably 16 mm wide, and most preferably 24 mm wide. The tensioning strip 20 may be applied to the liner at the trailing edge 34 or a position between the leading edge 35 and trailing edge 34 of the liner 16 in one of various ways. For example, the tensioning strip 20 may be removably applied to the liner 16 with use of a pressure sensitive adhesive or other similar pressure sensitive materials as previously described herein, or alternatively by a peelable thermal laminate. Further, for example, the tensioning strip may be permanently applied to the liner 16 using methods and materials similar to attachment of handles 18, 22.

Tensioning strip 20 may also be an additional release liner attached to release liner 16 using a suitable pressure sensitive adhesive such that when the additional release liner is removed an adhesive strip is revealed. The adhesive strip may be used to attach liner 16 after removal from flexible film 12 to other positions or instruments that require draping during surgery, as further described below.

FIGS. 5A–5F are detailed views of tensioning strip portions of alternative surgical incise drape configurations. As shown in the alternative drape configuration 80 of FIG. 5A, the tensioning strip 84 is permanently attached to the upper surface 87 of release liner 83. Further, the tensioning strip 84 may be permanently attached or releasably attached to flexible film 81 as the adhesive 82 coating the film 81 does not extend to the trailing edge of the film 81. If the tensioning strip 84 is permanently attached to flexible film 81, then portion 85 of the flexible film 81 at the trailing edge thereof may be detached with the tensioning strip 84 after application of the remainder of the flexible film 81 to a patient. Such detachment may be performed, for example, by cutting with a scissor, by tearing along a perforation 89 of the film 81, or by any other known detachment technique.

If the tensioning strip 84 is releasably attached such as with the use of a pressure sensitive adhesive, then the liner 83 with the tensioning strip 84 may be removed by peeling the liner 83 and tensioning strip 84 away from film 81. The film handle 86 is shown as being permanently attached to the film 81 and the liner handle 88 being integral with the release liner 83; however, any configuration for such handles as described herein may be utilized.

Figure 5A:
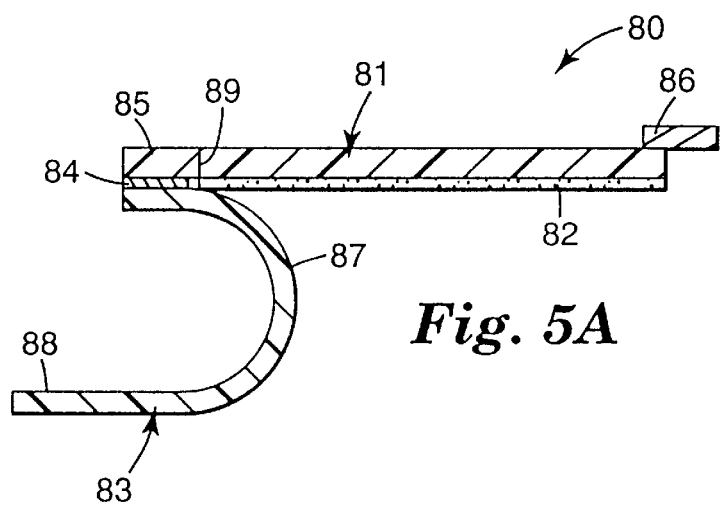
FIGS. 5A–5F are sectional views of the tensioning strip portions of alternative surgical incise drape configurations.
Figure 5B:
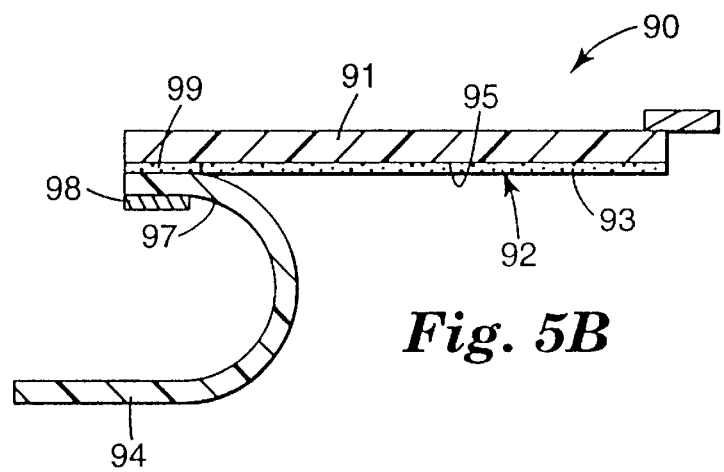

As shown in the alternative drape configuration 90 of FIG. 5B, the tensioning strip 98 is permanently attached to a lower surface 97 of release liner 94 at the trailing edge thereof. The liner 94 covers the pressure sensitive adhesive 92 coating the lower surface 95 of flexible film 91. The film handle and liner handle are shown in the same manner as shown in FIG. 5A. As described with reference to FIG. 5A, any handle configuration may be utilized.

Further as shown in FIG. 5B, the adhesive 92 on the flexible film 91 includes two regions of adhesive including adhesive region 93 and adhesive region 99. These two regions of adhesive 93, 99 require differential forces to peel the release liner 94 therefrom. For example, the combination of the adhesive region 93 and the liner 94 is such that the liner 94 may be peeled away from the adhesive region 93 with a force of less than about 120 g/cm, preferably less than about 80 g/cm, more preferably less than about 40 g/cm, and most preferably less than 25 g/cm, when measured in 180° peel at speed of 225 cm per minute. On the other hand, the force required to peel away the release liner 94 from the adhesive region 99 is such that the force required is distinguishable by the user from the force necessary to peel liner 94 away from the adhesive region 93. For example, the force required to remove the liner 94 from the adhesive region 99 may be a force greater than that required to peel away liner 94 from the adhesive region 93 by at least about 10%, preferably at least about 20%, and most preferably by at least about 30%.

The differential adhesive regions 93, 99 provide an indication to the user or applier of the drape that the user should stop peeling the liner 94 from the adhesive 92 and begin applying the adhesive region 93 and film 91 to the patient in a manner as described further below. Such a differential force technique may be utilized alone or in combination with other markers indicating this point in the process, e.g., markers 26 as shown in FIG. 2. The force required to remove the liner 94 from the adhesive regions 93, 99 can be changed by either modifying a characteristic of the adhesive regions 93, 99 or by modifying a characteristic of the liner 94. For example, the adhesive properties may be changed by changing the adhesive chemistry, changing the coating weight, or by heating the adhesive to better wet the liner. Further, for example, the liner characteristics may be changed by oxidizing the surface by processes such as corona discharge and flame treatment or by application of a coating, etc.

Figure 5C:
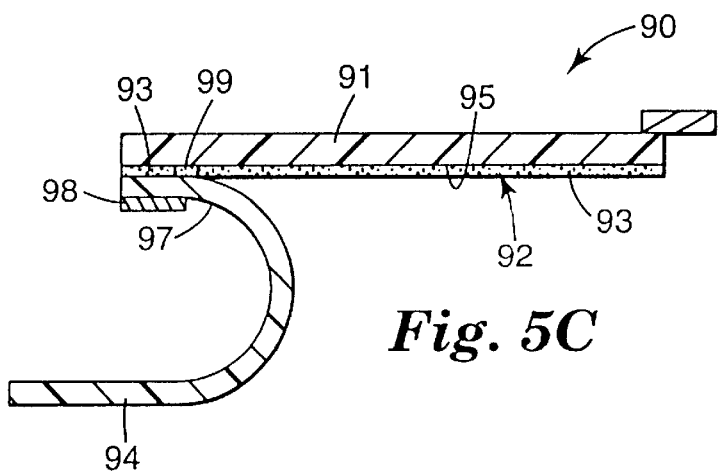

As shown in FIG. 5C, which is an alternative drape configuration to FIG. 5B, the higher force release region 99 need not extend to trailing edge of the film 91, and may take any form as long as the differential force function is provided. For example, the higher release region 99 may take the form of a strip between two lesser force regions 93 as shown in FIG. 5C. Further, the higher force region need not extend along the entire width (W) of the drape.

The differential forces for the regions 93, 99 may be provided by using a single adhesive with different release coatings applied to the adhesive or to the liner to achieve the differential adhesive characteristics, by using two different adhesives having different adhesive characteristics, or by thermally calendering or embossing the region 99 to increase the peel force of that region. However, the present invention is in no manner limited by such above listed techniques as any method known for providing differential adhesive characteristics for two regions may be utilized. Further, more than two differential adhesive regions may be used so as to provide the user with intermediate indications that the user is to stop peeling at some time quickly approaching.

In another preferred embodiment, the tension region or strip may be printed with appropriate information or symbols to provide an additional indication to the applier to stop removing the liner and apply the drape. The tension region or strip helps reduce wrinkling and bowing of the drape as the liner is removed during application.

Figure 5D:
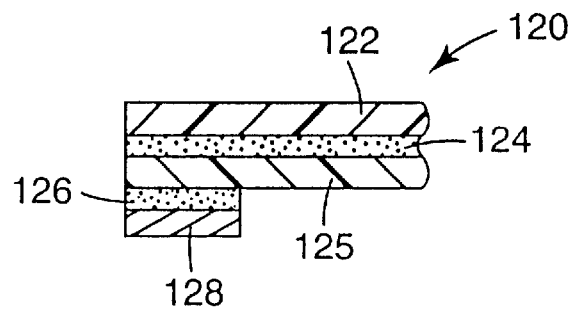

As shown in the alternative drape configuration 120 of FIG. 5D, tensioning strip 128 is removably attached to liner 125 by a pressure sensitive adhesive 126. As such, tensioning strip 128 can be removed exposing the adhesive 126. The liner 125 can be positioned using the adhesive 126 at another location to perform a drape function after the liner 125 is completely removed from the adhesive 124 coating the flexible film 122. Likewise, as described above with reference to FIG. 4A, the liner handle 45 may additionally or alternatively be removably attached using a pressure sensitive adhesive 49 applied to the liner 46 such that when the liner handle 45 is removed, the adhesive 49 is exposed. The liner 46 can then be used to drape another location by using the adhesive 49. For example, the liner 46 could be moved to another location of the patient, the surgical table, or instrument, such that another drape currently used for such purposes can be eliminated.

Figure 5E:
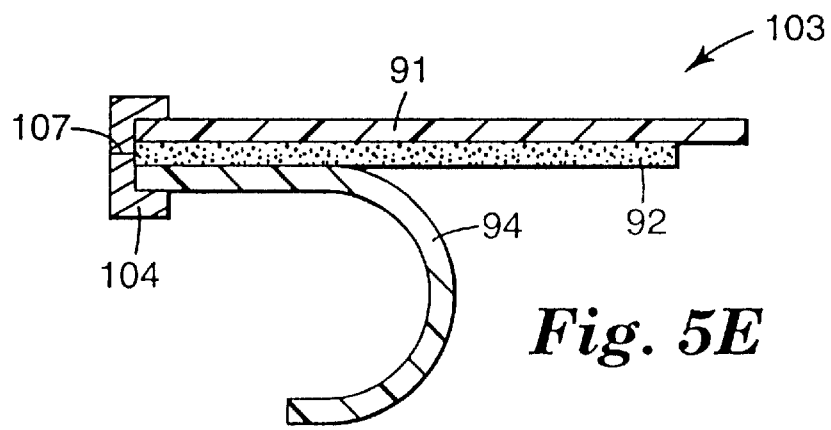

Further, alternatively, as shown by the drape configuration 103 of FIG. 5E, a tensioning strip 104 may be bonded to both liner 94 and film 91 such that the entire adhesive coating 92 can be exposed prior to application of the drape to the patient. Once applied, the liner 94 may be removed by tearing or removed using a releasable adhesive coating applied for adhering tensioning strip 104 to the film 91. If, for example, the tensioning strip 104 is formed of paper, tearing may be accomplished through ripping alone. Otherwise, tearing may also be accomplished using optional perforation 107.

Figure 5F:
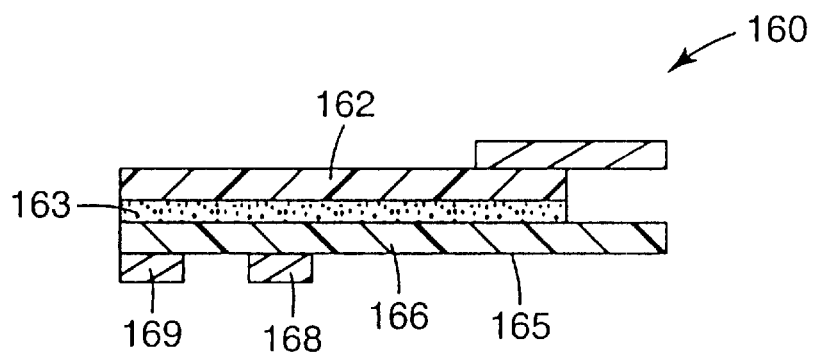

In yet another alternative drape configuration 160 of FIG. 5F, it is shown that one or more tensioning strips may be placed at positions other than at the trailing edge of the drape. As shown in FIG. 5F, the tensioning strip 168 is attached to a lower surface 165 of release liner 166 at a position between the leading and trailing edge of the release liner 166. Preferably, the tensioning strip 168 is positioned closer to the trailing edge than the leading edge and preferably extends along the entire width of the drape. The liner 166 covers the pressure sensitive adhesive 163 coating the lower surface of flexible film 162. The film handle and liner handle are shown in the same manner as shown in FIG. 5A.

As described with reference to FIG. 5A, any handle configuration may be utilized. With respect to embodiments such as shown in FIGS. 5B and 5C, tensioning strip 168 is advantageously placed at the point where adhesive section 93 meets section 99.

Alternatively, if tensioning strip 168 is sufficiently stiff relative to liner 166, a greater peel force will be required to remove the liner 166 from the adhesive 163 at the section thereof corresponding to the tensioning strip 168. Such a greater peel force is believed to be due from a significant change in the peel angle resulting from a much larger radius of curvature created as the relatively stiff tensioning strip is bent backwards as liner 166 is removed. In this manner, the tensioning strip 168 serves to both maintain the drape in a relatively flat and wrinkle free state while also alerting the clinician that sufficient adhesive coated area of the flexible film 162 has been exposed such that the drape can now be applied to the patient before the liner 166 is completely removed, e.g., a marker of when the user should stop peeling the liner 166 from the flexible film 162.

In addition, as shown in FIG. 5F, with a tensioning strip 168 being positioned somewhere between the leading and trailing edges of the liner 166, another tensioning strip 169 at the trailing edge of the liner 166 may also be utilized. Such additional tensioning strip 169 may be applied and positioned in any manner as described herein. It is readily apparent that any number of tensioning strips may be utilized in accordance with the present invention at various liner positions, and also that the present invention is in no manner limited to any particular number of tensioning strips at any particular liner positions.

Figure 8A:
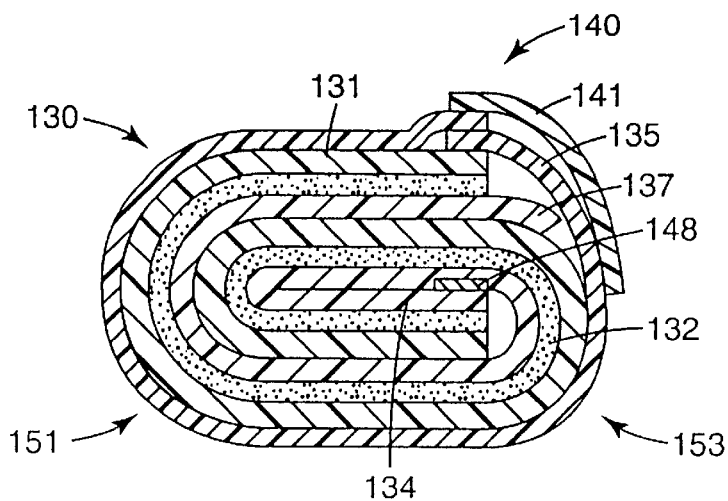
FIGS. 8A–8C are sectional views of alternative surgical incise drapes folded and having creases therein sufficient to prevent unrolling of the drape under its own weight.
Figure 8B:
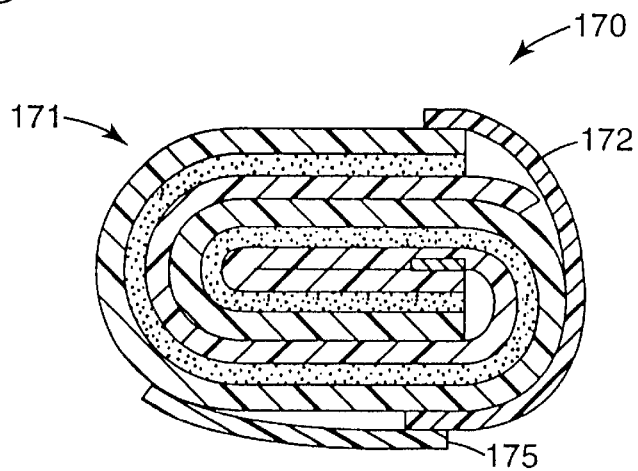
Figure 8C:
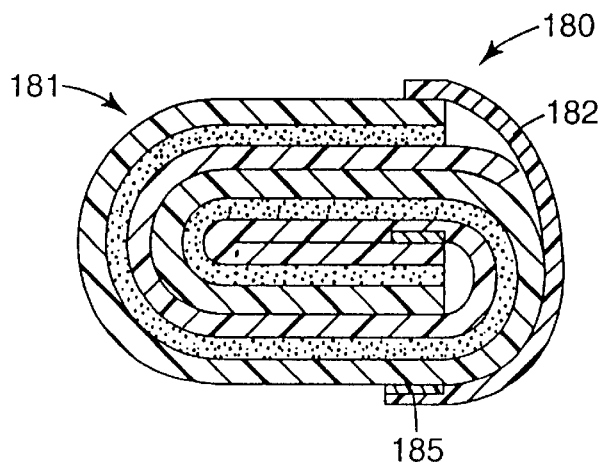

Positioning one or more tensioning strips in the middle of the drape as opposed to the trailing edge of the drape (and/or in addition to a tensioning strip at the trailing edge), has certain advantages in various circumstances. As described herein, the drape typically is provided to the user in a rolled or folded configuration. For example, rolled/folded configurations of drapes are shown in FIGS. 8A–8C. In many application techniques, the adhesive is exposed by grasping the handles and peeling a portion of the liner from the adhesive coating the film. The adhesive is then applied to the skin before the drape is completely unrolled. With the tensioning strip in the middle of the drape, tension is provided early in the application process such that wrinkles are prevented. Such an application technique is common when applying the drape to a limb. Locating the tensioning strip 168 in the interior of the drape, as shown in FIG. 5F, gives the drape stiffness in the center, the leading edge handle on the film 162 gives the drape stiffness at the leading edge, and the remaining rolled drape and additional trailing edge tensioning strip 169 gives stiffness to the trailing portion of the drape.

Figure 6:
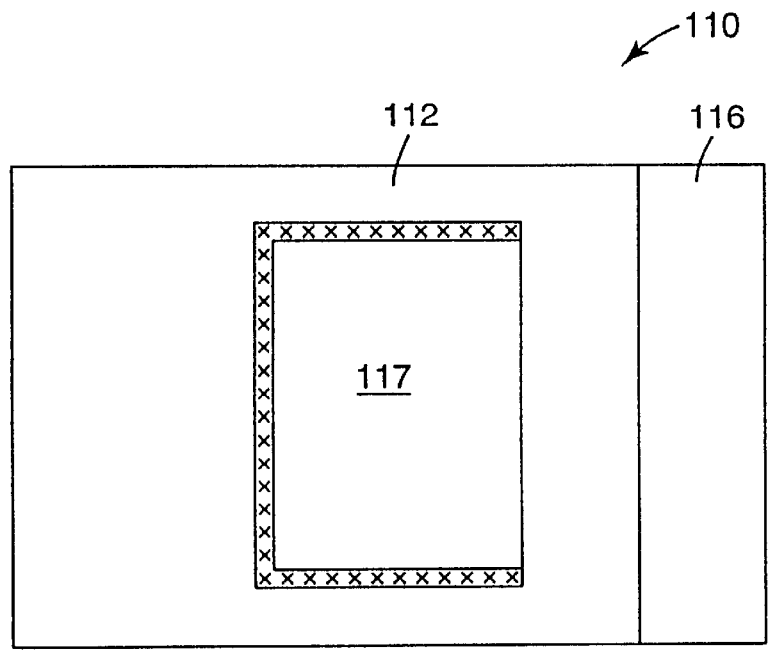
FIGS. 6 is a bottom liner-side plan view of an alternative surgical incise drape configuration having surgical attachments, e.g., pockets.

In an alternative surgical incise drape configuration as shown in FIG. 6, the liner 112 of the drape 110 having a liner handle 116 includes one or more attachments, generally represented by attachment 117. The attachments 117 may include pouches, tubing organizers, cautery holsters, instrument holders, fluid collection pouches, etc. The attachments may be formed, for example, by sealing a piece of plastic film, paper, or textile cloth to the surface of the liner 112.

It will be apparent to one skilled in the art that any of the configurations described herein, or portions thereof, including configurations of the film handle, liner handle, differential adhesive regions, and tensioning strips, may be used in any number of combinations in accordance with the present invention. For example, one drape configuration may use a film handle that may be removable by perforation, a liner handle that is integral with the liner, and a tensioning strip that is permanently attached to the liner; another drape configuration may use a film handle that is removable using releasable adhesive, a liner handle that is removable using releasable adhesive, and a tensioning strip that is removable from the liner using releasable adhesive. Another drape configuration may use a film handle that is removable, a permanently attached liner handle and a permanently attached tensioning strip.

The combinations are various and numerous and the present invention is only limited in accordance with the accompanying claims. Further, any of such configurations described herein, or portions thereof, may be used alternatively to portions of, or in combination with, drape 130 as shown in the alternative configuration described below with reference to FIG. 7.

Figure 7:
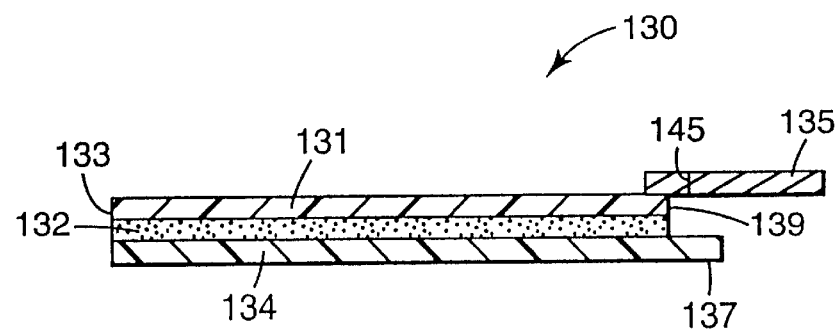
FIG. 7 is a sectional view of an alternative surgical incise drape wherein the liner itself provides the tensioning as opposed to the use of a tensioning strip associated with the liner.

With respect to the drape 130 of FIG. 7, the tensioning function is provided by the liner itself, without the need for a separate tensioning strip. In other words, the liner acts as the tensioning strip, i.e., provides a tensioning function during the entire removal and application process. However, one or more tensioning strips at various positions may be utilized to provide additional tensioning benefits. Drape 130 includes a liner 134 that is sufficiently stiff to help prevent wrinkling of flexible film 131 having adhesive 132 coated thereon during application. Preferably, liner 134 is a polyolefin liner having a thickness of at least about 50 microns, and more preferably a thickness of at least about 75 microns. For example, liner 134 may be a polypropylene liner, preferably a biaxially oriented polypropylene liner, of a thickness of at least about 75 microns, preferably of at least about 100 microns. Further, liner 134 may be a low or medium density polyethylene liner having a thickness of at least about 75 microns, preferably at least about 100 microns, or a high density polyethylene liner having a thickness of at least about 50 microns, preferably at least about 75 microns. Such liners preferably have an average stiffness as measured according to ASTM D4032-92 of at least about 2N, preferably at least about 3N, and more preferably at least about 4N.

The drape 130 further includes a film handle 135 that extends further beyond the leading edge 139 of the drape than liner handle 137, i.e., the film handle 135 is longer than the liner handle 137. As such, the film handle 135 may be used to protect the drape after rolling or folding of the drape, as previously mentioned with respect to film handle 18 shown in FIG. 1A, and which is described further below with reference to FIGS. 8A–8C. The handle protecting the drape when the drape is rolled or folded may be of any size or configuration adequate for providing such protection, e.g., the shape need not be rectangular, although such a shape is preferred to coincide with the shape of the drape.

Any of the surgical incise drape configurations previously described may be folded or rolled in any manner for packaging prior to delivery. Hereinafter, and as used in the accompanying claims, the term folding/folded used in conjunction with a drape includes the rolling of a drape or a rolled drape configuration. For example, a folded drape refers to a drape rolled around a core, a drape rolled without a core, a drape folded two or three times, etc. One illustrative folded configuration is shown and described further herein with reference to FIG. 8A.

The folded drape configuration 140 as shown in FIG. 8A includes drape 130 of FIG. 7 folded a number of times starting at the trailing edge 133 of the drape 130 and moving to leading edge 139. The drape 130 is folded with the flexible film 131 on the outside. The film handle 135 is of a size sufficient to extend around the entire outer periphery of the folded drape to protect the drape 130.

A closure tab 141 is provided for attachment to the film handle 135 and to portions of the drape 130 to hold the film handle 135 in place. As shown in FIG. 8A, the closure tab 141 is attached to the film handle 135 at two locations. The closure tab 141 may be any element releasable from the drape but sufficient to hold the film handle 135 in place about the periphery of the folded drape such that the folded drape is protected. The film handle 135 includes a perforation 145 for allowing the user to remove the handle 135 after the drape is applied to a patient, although any of the other handle removal techniques as previously described herein may be used.

Either the film handle or the liner handle of the liner can be made of a size to protect the folded drape. The drape 130 is folded starting at the trailing edge 133 of the drape 130 where an optional tensioning strip 148 may be positioned. Of course, a tensioning strip may be positioned at any location away from the leading edge 139 of the drape 130. Such an optional tensioning strip 148 may function as the "core" upon which the drape is rolled. Further, it is readily apparent that the drape 130 may be folded in such a manner that either the liner 134 or the flexible film 131 is to the outside.

Preferably, the folded drape configuration 140 is achieved by rolling and then subsequently flattening the rolled drape 130 such that creases at respective regions 151 and 153 are generated to maintain the drape in the generally flat folded configuration 140. If a paper liner is used, once the product is rolled up and compressed flat, permanent creases help prevent the product from unrolling prematurely such that it could flop down onto a non-sterile surface, e.g., the patient's skin. Preferably, the liner is stiff enough and the creases formed well enough that the drape will not unroll under its own weight.

With the use of a polymeric liner, such as a polyolefin liner, the liner is preferably sufficiently thick and the modulus of elasticity of the material sufficiently high so as to maintain such creases but avoid permanency of such creases. Such permanent creases are typical with conventional surgical incise drapes, such as those which use paper liners, that are folded and/or flattened prior to delivery. Such permanent creases result in irregular "bumping" and abrupt differences in force required as the drape is unrolled prior to or during application. This inconsistent delivery can lead to wrinkles. With the avoidance of such deep permanent creases, the polymeric liner provides for a delivered flexible film to the patient that in turn avoids such problems.

With liners that do not take a permanent, stable crease the drape may, in certain application techniques, tend to unroll prematurely. In this case, it is advantageous to apply a pressure sensitive adhesive either along the edges of the drape or within the interior of the drape. For example, a small amount of pressure sensitive adhesive may be exposed at the edges of the drape or may be deliberately applied to the edges of the drape that can be used to lightly bond the drape in the rolled or folded configuration.

Alternatively, a pressure sensitive adhesive may be applied in small zones on the top side of the film to bond the rolled or folded drape at strategic locations in order to prevent the drape from partially or fully unwinding prematurely during application. A particularly preferred adhesive for this purpose is 3M 9415 High Tack/Low Tack Double Coated Tape.

In another alternative, the edges of the drape may be lightly bonded using heat, e.g. a heated iron or hot air, in such a manner that the drape will not prematurely unwind but can still be easily unfolded during application. This method is particularly beneficial to products incorporating a polymeric liner.

In addition, with the use of a polymeric liner, such as a polyolefin liner (preferably a polyethylene liner), the surgical incise drape 140 can be folded to fit in packs and drawers without the liner tearing during application of the adhesive coated flexible film to the patient. On the other hand, paper liners appear to be affected by folds and permanent creases in the liner, which tend to lead to tear initiation and propagation. Further, the polymeric liner allows for the user to cut multiple layers of the drape into a desired size and shape. This is typically difficult to perform with use of a heavy paper liner. Further, once the drape has been rolled, the drape using the plastic liner can be flattened under pressure and/or heat to ensure sufficient creasing.

Alternatively, as shown in the drape configuration 170 of FIG. 8B, the handle 172 may be of a size such that the handle 172 does not wrap entirely around the periphery of the drape 171. A closure tab 175 is positioned for holding the handle 172 in place such that the drape 171 remains in a folded configuration. Alternatively, other means of providing closure may be used to hold the drape in a folded configuration. For example, a paper or plastic sheet may be wrapped about the folded drape as an overwrap. Further, as shown in the drape configuration 180 of FIG. 8C, an extended handle 182 may have a portion coated with a pressure sensitive adhesive 185 for attachment to a portion of the drape 181 for holding the handle 182 in place such that the drape 181 remains in a folded configuration. Generally, in such drape configurations 170, 180, the handles are of a adequate size and are attached by some technique to another portion of the drape to maintain the drape in the folded configuration.

Generally, the drape configurations, as described herein, maintain a flexible film in a wrinkle free state as a liner is peeled away and the flexible film is applied to a patient as described below. The various drape configurations can be applied to a patient in a number of ways. First, the application of the drape 10 shown in FIGS. 1–3 shall be described. Thereafter, the application of the drape 130 shall be described. FIG. 1A and FIGS. 2 and 3, illustrate the surgical incise drape 10 prior to starting the application procedure. FIG. 1B illustrates the beginning of the removal of the release liner 16 from the adhesive 14 coating the film 12. To start the application process, a user grasps the film handle 18 and another user grasps the liner handle 22 of a rolled drape. An illustrative example of a rolled drape is shown in FIG. 8A.

After the drape 10 is at least partially unrolled, the release liner 16 is then further peeled back from the adhesive 14. As illustrated in FIG. 1C, the release liner 16 is peeled back such that the trailing edge 34 of the release liner 16 is still attached to the adhesive 14 at the trailing edge 32 of the film 12. At this point the flexible film 12 is ready for application to the patient. The user may be signaled to stop unrolling the release liner from the adhesive 14 in a number of ways. For example, as shown in FIG. 2, the flexible film 12 may have markings 26 to indicate to the user the point at which the user is to stop unrolling and proceed to application of the film 12 to the patient. Further, the indication to stop unrolling may be provided, for example, using a technique as described with reference to FIG. 5E. Alternatively, the indication may be provided using differential adhesive regions as described above with reference to FIGS. 5B and 5C; the differential regions providing the user with a recognizable differential force at a point during the removal of the release liner 16, i.e., the force required to remove the liner 16 changes at the mark 26.

As shown in FIG. 1D, the user, preferably, holds the surgical incise drape 10 with the liner partially removed such that the flexible film 12 having the adhesive 14 coated thereon is in a relaxed substantially "U," i.e, "saddle" type, configuration. The U type configuration has a lower center adhesive portion 37 for initial contact with and adherence to the patient, such as, for example, on the chest or back of the patient. With the lower center portion 37 contacting and adhering to the patient, the remainder of the flexible film 12, i.e., the flexible film on each side of the center portion 37, is smoothed onto the surface of the patient.

It should be apparent that in many circumstances a U type configuration is not used. For example, when application of the drape is to a limb, only a small portion of the adhesive 14 may be exposed prior to application of the adhesive to the limb. Thereafter, the adhesive is further unrolled and applied to the limb.

After the film 12 is smoothed onto the patient, the remainder of the release liner 16 is then removed from the flexible film 12 and adhesive 14. As such, the flexible film 12 provided with the handle 18, as shown in FIG. 1E, is applied to the patient in a substantially wrinkle free condition. Further, after application, the drape has only one handle 18 remaining. The handle 18 may then be removed from the flexible film 12, such as, for example, with the use of a releasable adhesive or perforation. With only one handle 18 left on the drape 10 to remove after application of the film 12 to the patient, process steps for using the drape is reduced relative to other drape application techniques, such as techniques using two handles.

With the use of a clear polymeric liner, users who apply the drape can more easily see the field upon which the drape 10 is being applied. The advantage of a clear polymeric liner is shown by the illustration of FIG. 1D. When the users hold the drape 10 in this substantially U type configuration, it clearly is advantageous to see through the liner during application to the patient.

FIG. 8A illustrates the surgical incise drape 130 prior to starting the application procedure. The surgical incise drape 130 as shown in FIG. 8A would typically be contained within a disposable, protective bag (e.g., made from polyethylene). The film handle 135 wrapped about the periphery allows the drape 130 to be easily inserted within a protective bag during packaging. Further, the film handle 135, prevents the insertion process from damaging the drape. For example, without a protective covering, e.g., a wrapped film handle 135 or an undesired separate protective covering, a portion of the drape may catch on the protective bag during insertion therein resulting in a disconfigured drape, e.g., a torn liner, a wrinkled film, etc. A separate protective covering is undesirable because of the added waste of an additional separate material. By using the film handle 135 (or alternatively an extended liner handle), as the protective covering, a separate piece of waste is eliminated.

After removal of the drape 130 from the protective bag (not shown), a user removes the closure tab 141. The user then grasps the film handle 135 and unwraps the film handle 135 from the remainder of the drape 130 exposing the liner handle 137. Another user then grasps the liner handle 137 of the folded drape. The release liner 134 is then peeled back from the adhesive 132. The users may peel back the liner 134 as far as desired, but with a portion of the liner 134 still attached to the adhesive 132. The user may be signaled to stop unrolling the release liner 134 in the same manner as described above with reference to FIG. 1.

At any time when the adhesive 132 is exposed, the adhesive coated flexible film 131 is ready for application to the patient. After a major portion of the adhesive 132 is exposed and the flexible film 131 is smoothed onto the patient, the remainder of the release liner 134 is then removed from the flexible film 131 and adhesive 132. As such, the flexible film 131 provided with the handle 135 is applied to the patient in a substantially wrinkle free condition. Further, after application, the drape has only one handle 135 remaining. The handle 135 may then be removed from the flexible film 12, such as, for example, with the use of perforation 145.

As shown in FIGS. 2 and 3, one or more of the handles 18, 22, or tensioning strip 20 may have printed information 24 thereon. For example, the printed information 24 may include instructions for using the drape 10 or any other information. This reduces the amount of packaging necessary for the drape 10. Preferably, the printed information 24 is placed on the handle attached to the film 12 so that it is in view for a greater period of time during the application process and serves to indicate which side should be "up" during application.

Further, in accordance with the present invention, the film, the liner, the adhesive, or any combination of such elements, may be treated to ensure the drape does not have excessive static. Preferred drapes have a surface resistivity of less than about $10^3$ ohms, preferably less than about $10^{12}$ ohms, and most preferably less than about $10^{11}$ ohms as measured using a Keithley Model 487 picometer voltage source set to 500 volts with a Keithley Model 8008 Resistivity Test Fixture. This may be achieved by addition of hydrophilic or conductive agents to the adhesive such as salts, glycols, hydrophilic polar substituents of the adhesive itself (e.g., in an acrylate adhesive one may incorporate monomers such as acrylic acid and its derivatives, acrylamide and its derivatives, N-vinyl lactams, hydroxyalkylacrylates and its derivatives including polyethoxylated hydroxyalkylacrylates and the like; in a polyurethane adhesive the adhesives may contain hydrophilic polyols such as polyethylene glycol and copolymers of ethylene oxide and propylene oxide). Alternatively or additionally, antistatic agents may be applied to or incorporated into the flexible film and/or the liner. Suitable antistatic agents include nonionic, anionic, cationic and zwitterionic surfactants as well as hydrophilic or conductive polymers.

Figure 9:
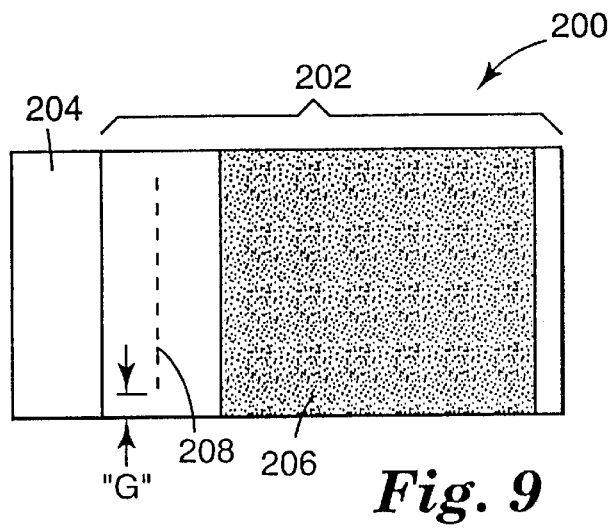
FIG. 9 is a bottom plan view of yet another embodiment of a surgical incise drape with handle incorporating a tear line.

FIG. 9 shows yet another embodiment of the drape 200. The drape 200 comprises film backing 202, which is coated with adhesive 206 along one major surface thereof, and handle 204. A tear line 208 (e.g., a line of perforations) is provided, with the perforations 208 spaced from the edges of the film backing 202 by a margin or gap G.

As described previously, the flexible film backing 202 is preferably elastomeric and very thin, often having a thickness of less than about 75 microns and preferably less than about 52 microns. Since the flexible film 202 is so thin, if the film is perforated all the way to the edge of the film or if a notch is placed in the edge of the film forces exerted during application may result in the perforation tearing during application. Therefore, it would be desirable to have a section of drape at the edges that resists tearing but may be torn under sufficient force followed by a easily propagated tear line. In order to prevent an undesirable tear at the perforation from occurring during application a section G of non-perforated film preferably is left at the margins of the drape. In this manner, the drape is robust and the perforation will not start until a significant shear force is applied such as would occur when one deliberately would like to remove the handle. Preferably the margin G of non-perforated film at the film edge is at least 0.5 cm, more preferably at least 1 cm, and most preferably at least 2 cm, e.g. a margin of about 2.5 cm has been shown to work well.

Alternatively, the resiliently-flexible film may be perforated completely to the edge and a reinforcement applied at the edge such as a piece of tearable tape to reinforce this section (e.g., the same area shown at "G" in FIG. 9). The reinforcement "tape" may be a piece of adhesive coated paper, plastic, or other material that resists the stresses which occur during application but may be torn when the clinician wants to remove the handle 204.

Figure 10:
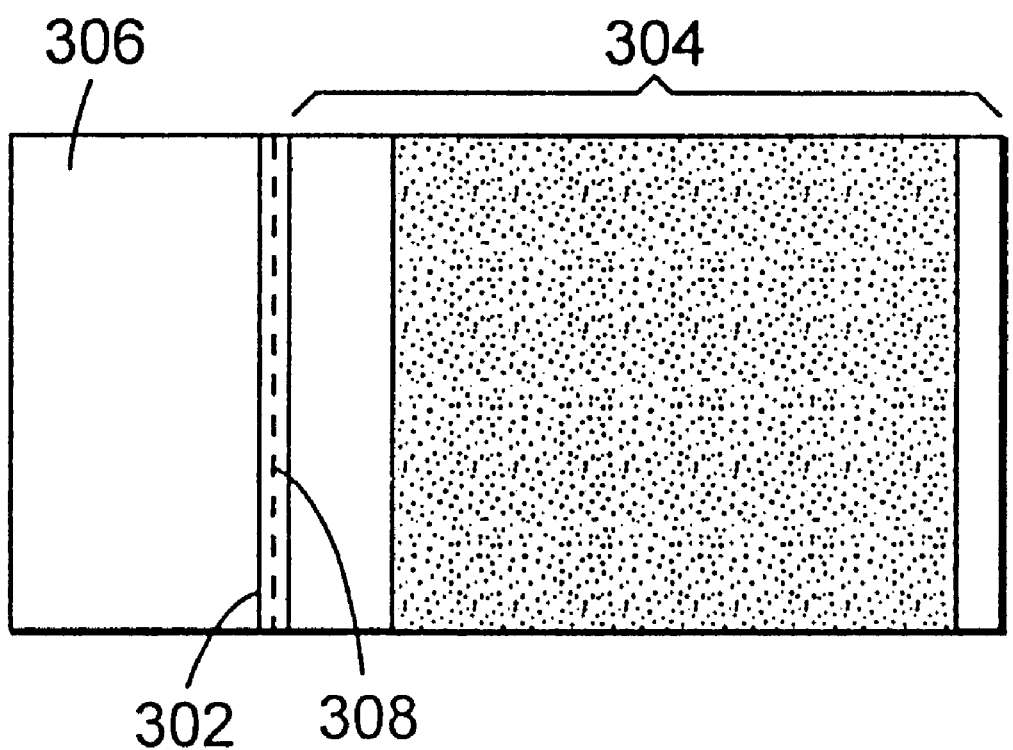
FIG. 10 is a bottom plan view of yet another embodiment of a surgical incise drape with handle releasably held in place by perforated tape.

As shown in FIG. 10, the drape 300 may include a reinforcement tape 302 extending the full width of the drape. The reinforcement tape 302 is bonded to the film 304, the film handle 306, or preferably to both to bridge or connect the film 304 and the film handle 306. The reinforcement tape 302 preferably has a plurality of perforations 308 forming a tear line, although it is contemplated that the tear line could be formed by other suitable means, such as by scoring the tape along its length or providing a longitudinally-extending zone of weakness.

While the film and film handle may overlap, the reinforcement tape 302 preferably is positioned to connect or bridge the film 304 and the film handle 306 so that no overlap occurs. The line of perforations 308 is preferably located in the reinforcement tape 302 between the film 304 and the film handle 306 so that when the line of perforations 308 is torn neither the film 304 nor film handle 306 are torn.

In a preferred embodiment, the perforated reinforcement tape 302 is a perforated low-density polyethylene film tape with acrylate adhesive, such as the tape available from Minnesota Mining and Manufacturing under the trade designation "3M Transpore™" tape. This preferred "3M Transpore™" tape has multiple lines of perforations can be used to attach the film handle to the film with no overlap. In this manner, the handle is removed cleanly by tearing through the perforated tape.

The unperforated margin G and the reinforcement tape constitute exemplary embodiments of means for resisting tearing adjacent the edge of the drape. The line of perforations constitute one embodiment of a tear line or means for propagating tearing along a line. Alternative embodiments of this tear line or means for propagating tearing along a line include scoring the film along the line, decreasing the thickness of the film along the line, e.g., by using heat and compression, or providing any suitable configuration of perforation.

Co-assigned U.S. patent application Ser. No. 08/857,723, filed May 16, 1997; Ser. No. 08/648,786, filed May 16, 1996; and Ser. No. 08/857,724, filed May 16, 1997, disclose surgical incise drapes and are incorporated herein by reference.

The patents, patent documents, and publications cited herein are incorporated by reference in their entirety, as if each were individually incorporated by reference. Various modifications and alterations of this invention will become apparent to those skilled in the art without departing from the scope of the invention, and it should be understood that this invention is not to be unduly limited to the illustrative embodiments and methods set forth herein.

What is claimed is:

1. A surgical incise drape comprising:
    a flexible film having a major portion coated with an adhesive, the flexible film having a leading edge and a trailing edge; and
    a liner having a leading edge and a trailing edge corresponding to the leading edge and trailing edge of the flexible film, the liner substantially covering the major portion of the flexible film coated with the adhesive, and the liner being a laminate film comprising two or more polymer layers.

2. The drape according to claim 1, wherein the laminate film includes at least one low melting point polymer layer and at least one high melting point polymer layer.

3. The drape according to claim 2, wherein the at least one low melting point polymer layer has a melt temperature less than about 175° C.

4. The drape according to claim 3, wherein the at least one low melting point polymer layer is a polyolefin layer.

5. The drape according to claim 2, wherein the at least one high melting point polymer layer has a melt temperature greater than about 175° C.

6. The drape according to claim 5, wherein the at least one high melting point polymer layer is a polyester or cellulose acetate layer.

7. The drape according to claim 5, wherein the at least one high melting point polymer layer is a polyamide layer.

8. The drape according to claim 7, wherein the liner is relatively stiff compared to the flexible film such that the liner holds the flexible film in a wrinkle-free state when the liner is being removed from the major portion of the flexible film.

9. The drape according to claim 1 further comprising an elongate strip along the leading edge of the film, the strip having a tear line for facilitating propagating tearing of the strip along the tear line.

10. The drape according to claim 9 wherein the tear line comprises a line of perforations.

11. The drape according to claim 9 wherein the elongate strip comprises reinforcement tape that is more resistant to tearing than the film other than along the tear line.

12. The drape according to claim 11 wherein the reinforcement tape is a film tape having one surface coated with an adhesive.

13. The drape according to claim 12 wherein the adhesive comprises a pressure sensitive adhesive.

14. The drape according to claim 11 wherein the film tape comprises a low-density polyethylene film tape, and the adhesive comprises an acrylate adhesive.

15. A medical composite article comprising:
    a flexible film having a major portion coated with an adhesive; and
    a liner substantially covering the major portion of the flexible film coated with the adhesive, and the liner being a laminate film comprising two or more polymer layers, the laminate film including at least one low melting point polymer layer and at least one high melting point polymer layer.

16. The medical composite article according to claim 15, wherein the at least one low melting point polymer layer has a melt temperature less than about 175° C.

17. The medical composite article according to claim 16, wherein the at least one low melting point polymer layer is a polyolefin layer.

18. The medical composite article according to claim 15, wherein the at least one high melting point polymer layer has a melt temperature greater than about 175° C.

19. The medical composite article according to claim 18, wherein the at least one high melting point polymer layer is a polyester or cellulose acetate layer.

20. The medical composite article according to claim 18, wherein the at least one high melting point polymer layer is a polyamide layer.

21. The medical composite article according to claim 15, wherein the liner is relatively stiff compared to the flexible film such that the liner holds the flexible film in a wrinkle-free state when the liner is being removed from the major portion of the flexible film.

22. A medical composite article comprising:
   a flexible film having a major portion coated with an adhesive; and
   a liner substantially covering the major portion of the flexible film coated with the adhesive, and the liner being a laminate film comprising two or more polymer layers, the laminate film including at least one low melting point polymer layer having a melt temperature less than about 175° C. and at least one high melting point polymer layer having a melt temperature greater than about 175° C.

23. The medical composite article according to claim 22, wherein the at least one low melting point polymer layer is a polyolefin layer.

24. The medical composite article according to claim 22, wherein the at least one high melting point polymer layer is a polyester or cellulose acetate layer.

25. The medical composite article according to claim 22, wherein the at least one high melting point polymer layer is a polyamide layer.

26. The medical composite article according to claim 22, wherein the at least one low melting point polymer layer is a polyolefin layer, and the at least one high melting point polymer layer is a polyester or cellulose acetate layer.

27. The medical composite article according to claim 22, wherein the at least one low melting point polymer layer is a polyolefin layer, and the at least one high melting point polymer layer is a polyamide layer.

28. A medical composite article comprising:
   a flexible film having a major portion coated with an adhesive, the flexible film having a leading edge and a trailing edge;
   an elongate strip along the leading edge of the film, the strip having a tear line for facilitating propagating tearing of the strip along the tear line; and
   a liner substantially covering the major portion of the flexible film coated with the adhesive, and the liner being a laminate film comprising two or more polymer layers, the laminate film including at least one low melting point polymer layer having a melt temperature less than about 175° C. and at least one high melting point polymer layer having a melt temperature greater than about 175° C.

29. The medical composite article according to claim 28 wherein the tear line comprises a line of perforations.

30. The medical composite article according to claim 28 wherein the elongate strip comprises reinforcement tape that is more resistant to tearing than the film other than along the tear line, the reinforcement tape being a film tape having one surface coated with a pressure sensitive adhesive.

31. The medical composite article according to claim 30 wherein the film tape comprises a low-density polyethylene film tape, and the pressure sensitive adhesive comprises an acrylate adhesive.

* * * * *